(12) United States Patent
Jochens

(10) Patent No.: US 6,814,279 B2
(45) Date of Patent: Nov. 9, 2004

(54) CRICKET BOX

(76) Inventor: James M. Jochens, 8530 Valcour, St. Louis, MO (US) 63123

(*) Notice: Subject to any disclaimer, the term of this patent is extended or adjusted under 35 U.S.C. 154(b) by 41 days.

(21) Appl. No.: 10/279,308

(22) Filed: Oct. 23, 2002

(65) Prior Publication Data

US 2004/0020976 A1 Feb. 5, 2004

(51) Int. Cl.[7] ................................................ B65D 5/00
(52) U.S. Cl. ..................... 229/120.1; 229/178; 229/122; 229/172; 229/244
(58) Field of Search ................................ 229/243, 244, 229/120.1, 172, 120, 122, 178

(56) References Cited

U.S. PATENT DOCUMENTS

| | | | | |
|---|---|---|---|---|
| 1,956,444 A | * | 4/1934 | Hewitt | 229/120 |
| 2,266,649 A | * | 12/1941 | Marshall | 229/243 |
| 2,719,665 A | * | 10/1955 | Tharpe et al. | 229/117.09 |
| 3,301,461 A | * | 1/1967 | Kroeschell | 229/117.17 |
| 3,949,931 A | * | 4/1976 | Hall | 229/102 |
| 4,082,215 A | * | 4/1978 | Eichenauer | 229/120 |
| 4,168,028 A | * | 9/1979 | McCall | 229/147 |
| 4,513,907 A | * | 4/1985 | Grosshuesch | 229/120 |
| 5,007,580 A | * | 4/1991 | Morrison et al. | 229/117.17 |
| 5,197,659 A | * | 3/1993 | Vassiliou | 229/117.01 |
| 5,772,107 A | * | 6/1998 | Younger | 229/122.27 |
| 6,151,211 A | * | 11/2000 | Dayan et al. | 361/690 |
| 6,491,212 B1 | * | 12/2002 | Militzer | 229/125.125 |

* cited by examiner

Primary Examiner—Tri M. Mai
(74) Attorney, Agent, or Firm—Polster Lieder, et al.

(57) ABSTRACT

A cricket box has a bottom wall; a top wall; a rear wall integral with the bottom and top walls; a front wall integral with the bottom wall, and side walls integral with the bottom wall. Each of the side walls has at least one substantial opening in it. The rear and front walls have end flaps at each end, folded inwardly substantially perpendicularly to the front and rear walls and bottom wall to lie alongside and inboard of the side walls, the end flaps having openings complementary to the side wall opening or openings. The side walls have side wall panels folded over the end flaps, those panels having openings complementary to the opening or openings in the side walls and the end flaps. The side wall panels engage the bottom wall along their outer edges, and cage a screen between the side wall panels and the end flaps. The screen extends over the opening or openings.

9 Claims, 4 Drawing Sheets

CRICKET BOX

CROSS REFERENCE TO RELATED APPLICATIONS

STATEMENT REGARDING FEDERALLY SPONSORED RESEARCH OR DEVELOPMENT

Not Applicable

BACKGROUND OF THE INVENTION

Although the box of this invention is described as being used for the transport of crickets, the term "Cricket Box" as applied to the box of this invention is not intended to be limited to a box used in the shipment of crickets. The "cricket box" of this invention can be used in shipping such insects as ladybugs, hover flies, yellow jackets, ground beetles, and mealworms, just as examples. It can also be used to transport small animals.

Millions of crickets are shipped every year, not only for bait but, more frequently, for food for reptiles of various sorts. Boxes presently commercially available for shipping crickets have front, back, and side walls each with panels that fold in, one set of panels overlapping the other with the meeting edges of one set crossing the meeting edges of the other at right angles. Side walls of the box have openings in them, closed by screen wire each stapled in place by 15 or more staples, for a total of at least 30 staples. The exposed edges of the flaps are taped to hold them in position and also to prevent the escape of the crickets (or other insects). The boxes presently used are subject to being crushed, and are labor intensive, requiring, as they do, that the screen be stapled, a hand operation, and extensively taped, also a hand operation.

The box of this invention requires no staples or glue, and little taping. Its sidewalls are effectively three-ply, giving great resistance to crushing, so that the boxes not only can be shipped with less damage, but can be stacked vertically to almost any height to which such boxes are likely to be stacked. Their blanks are not complicated, and their assembly is relatively fast and easy, reducing the labor required by orders of magnitude.

BRIEF SUMMARY OF THE INVENTION

In accordance with this invention, generally stated, a cricket box has a bottom wall, a top wall, a rear wall integral with the bottom wall along a bottom edge and integral with the top wall along a upper edge, a front wall integral with the bottom wall along a bottom edge, and sidewalls integral with the bottom wall on a bottom edge. Each of the sidewalls has at least one substantial opening in it. The rear and front walls have end flaps at each end, folded inwardly substantially perpendicularly to the front and rear walls and to the bottom wall, to lie along side and inboard of the sidewalls. The end flaps have openings complementary to the sidewall openings. The sidewalls have sidewall panels integral with the sidewalls, folded over the end flaps. The sidewall panels have openings complementary to the openings. The sidewall panels engage the bottom wall, and in the preferred embodiment, have a strip from which locking tabs are lanced, the locking tabs engaging lips defining one edge of slits in the bottom wall, the strips engaging the bottom wall.

BRIEF DESCRIPTION OF THE SEVERAL VIEWS OF THE DRAWINGS

The objects of the invention are achieved as set forth in the illustrative embodiments shown in the drawings which form a part of the specification.

DETAILED DESCRIPTION OF INVENTION

Figure 1:
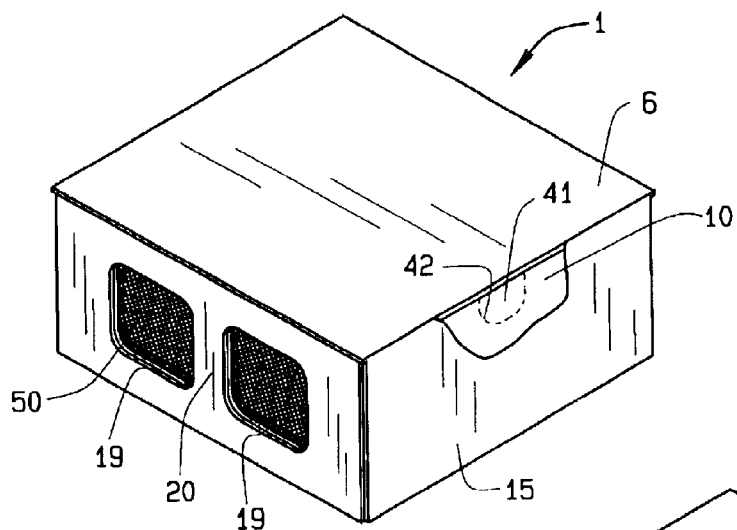
FIG. 1 is a view in perspective of one embodiment of box of this invention, partly cut away, viewed from the top, a front and one side.
Figure 2:
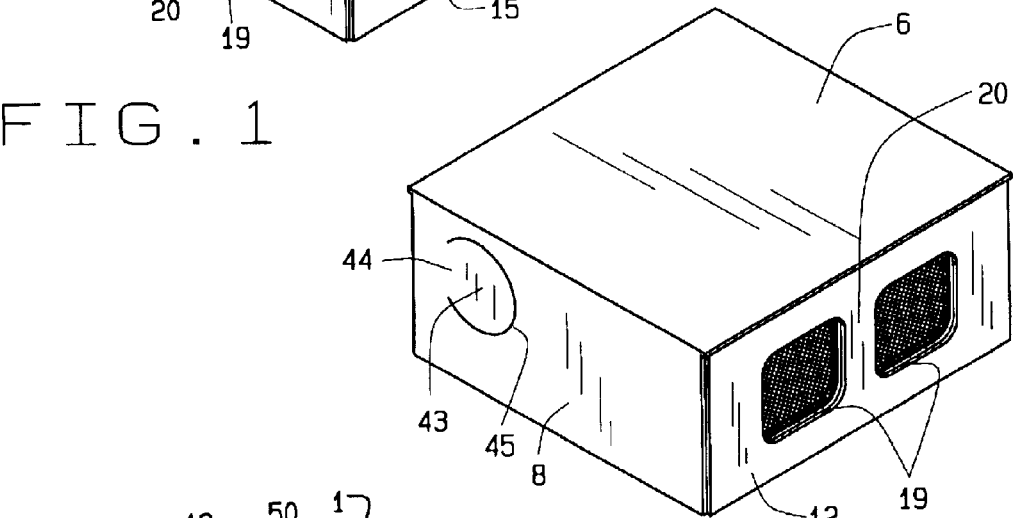
FIG. 2 is a view in perspective of the box of FIG. 1, viewed from a rear and side.
Figure 3:
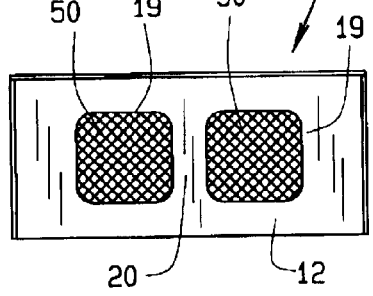
FIG. 3 is a view in side elevation.
Figure 4:
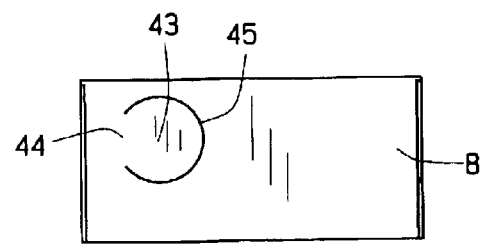
FIG. 4 is a view in rear elevation.

The following detailed description illustrates the invention by way of example and not by way of limitation. This description will clearly enable one skilled in the art to make and use the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

Referring now to the drawings for one illustrative embodiment of box of this invention, reference numeral 1 indicates an assembled box. The box is preferably made of corrugated board, B flute or C flute, but other types of board can be used. The box 1 has a bottom wall 4, in which slits 5 are made, a top wall 6, a rear wall 8, a left side wall 12 and a right side wall 13, and a closure panel 15, integral with the top wall 6. The closure panel 15 has tuck-in tabs 17 at either side. Strips of tape can be applied to outer side edges of the top wall 6 to ensure that no gap develops along those edges, and a short piece of tape applied extending between the closure panel and the front wall as additional insurance against accidental opening of the closure panel.

The side walls 12 and 13 have in them openings 19, between which, on each side, a column 20 of uncut board is left. Intermediate its length, each of the side walls has spaced parallel inner and outer score lines 21 and 22, which may take the form of short slits in one or both of the facing sheets, defining a hinge area 23. A side wall panel 24 is attached to each side wall along the outer score line 22. The side wall panel 24 has at its outer end a strip 26, from which locking tabs 27 are lanced, as shown particularly in FIG. 7. When the strip 26 is folded as shown in FIG. 6, the locking tabs 27 project freely from the side wall panel.

Figure 6:
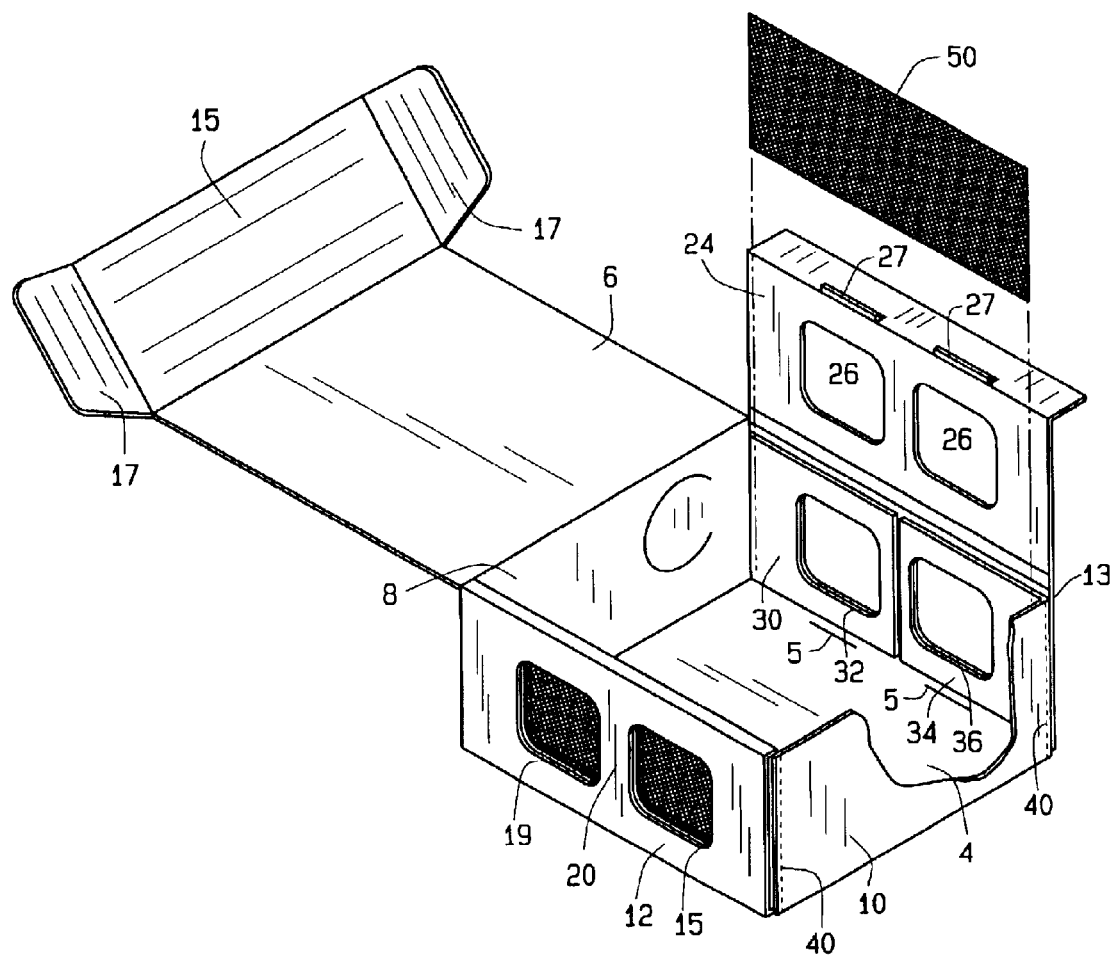
FIG. 6 is a view in perspective corresponding to the view in FIG. 5, but with a side wall panel unfolded and one set of front wall and rear wall end flaps in position and a screen before its installation.
Figure 7:
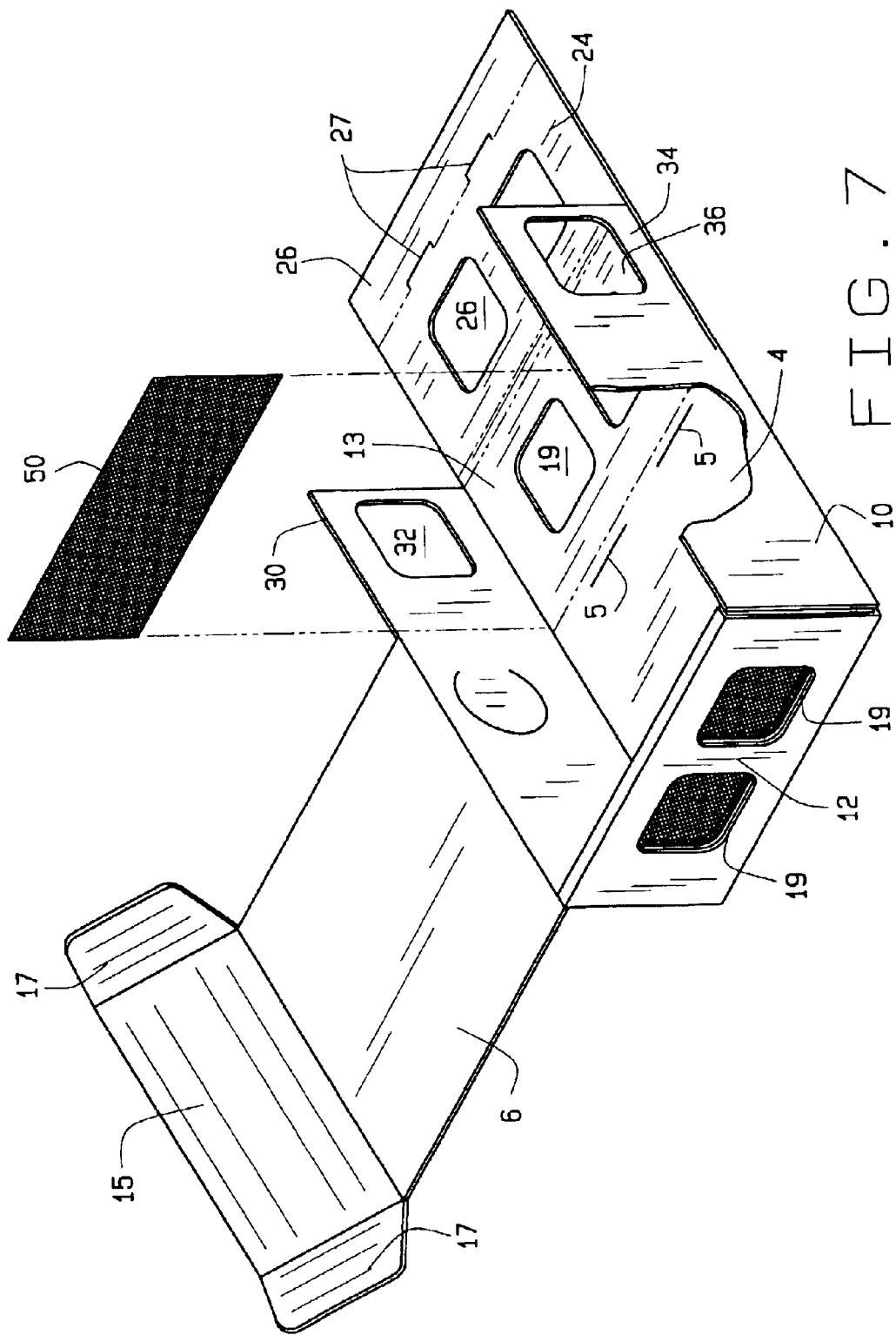
FIG. 7 is a view in perspective corresponding to the view in FIG. 6, with front wall and rear wall end flaps unfolded and a side wall, side wall panel and strip unfolded and lock tabs unexposed.

The rear wall 8 has at two ends, rear wall end flaps 30, each with an opening 32 corresponding to the nearest of the openings 19 in the adjacent side wall, as shown in FIGS. 6 and 7. Similarly, the front wall 10 has at two ends, front wall end flaps 34, each with an opening 36 corresponding to the nearest of the openings 19 in the adjacent side wall, also as shown in FIGS. 6 and 7. The structure of the side wall 12, and its side wall panel, strip and locking tabs, shown as fully assembled in FIGS. 6 and 7, is identical to the side wall 13 and its associated parts.

The rear and front wall end flaps are folded in until they are at right angles to their respective walls, and to the bottom wall, as shown in FIG. 6. A rectangular screen 50, shaped to fit closely between the front and rear walls, as shown in FIG. 6, is then put in place over the folded flaps 30 and 34, the side panels are folded along the score lines 21 and 22, which are spaced to permit the side panels to cage the screen snugly against the flaps 30 and 34, and pushed at their bottoms, folding the strips 26 against the bottom wall, until the locking tabs, deflecting downwardly the area between the slits and the flaps, engage a lip formed on the other side of the slits, so that the side panels are now held both frictionally and positively in position.

Figure 5:
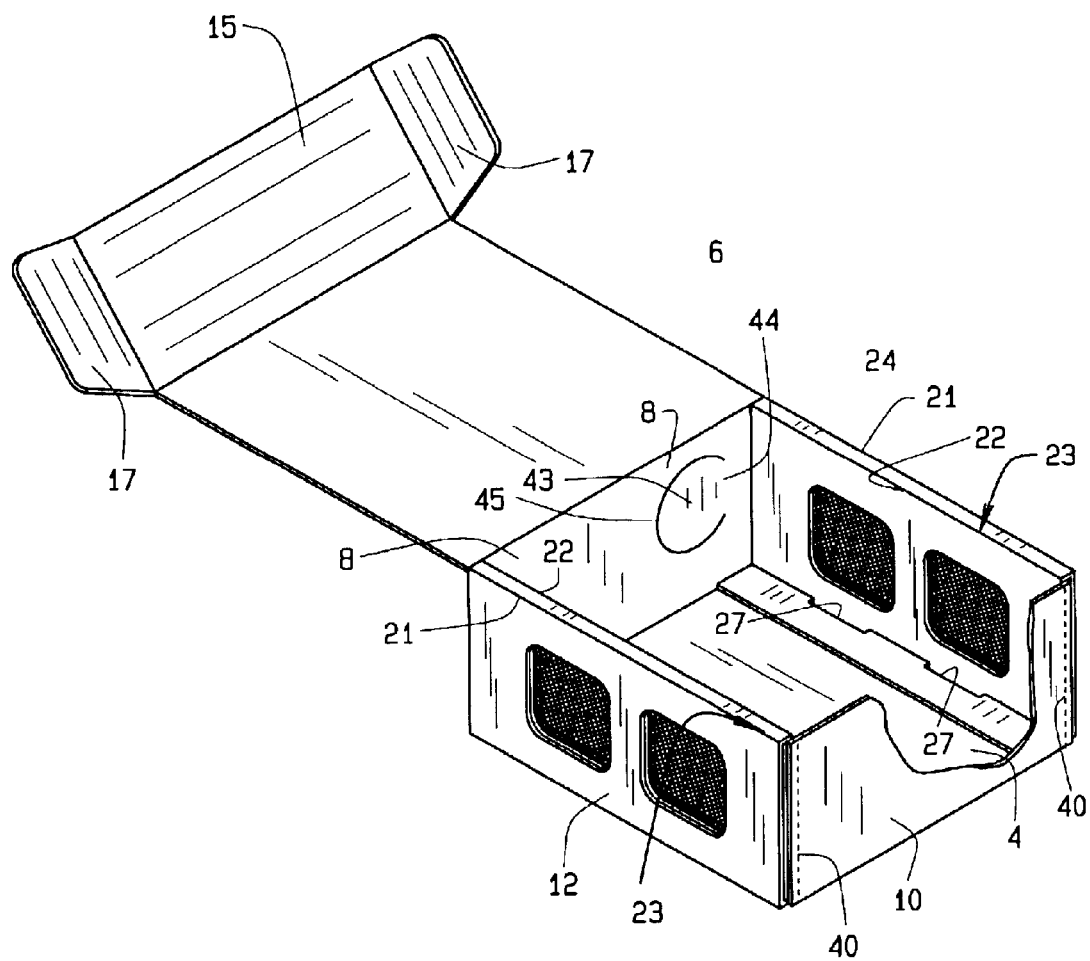
FIG. 5 is a view in perspective, partly broken away, of the box with the top and a closure flap laid back showing a side wall panel, strip and locking tabs in assembled condition.

As shown particularly in FIGS. 5, 6 and 7, the top wall 6 is integral with the rear wall 8 along a fold line, to fold tightly over the side walls 12 and 13 when brought from the position shown in FIGS. 4–7, to a position overlying what are now the side wall top edges. The closure panel is now folded over the front wall, and the tuck-in tabs 17 are inserted between the side walls and the front wall enc flaps, where they are held firmly.

In the preferred embodiment shown, the front wall 10 has tear lines 40 near both side corners, running from the bottom wall up to the free top edge of the wall, and a finger opening area 41, defined by a cut line 42, that can be pushed out with one's finger to facilitate tearing of the front wall along the tear lines, to permit the contents of the box to be dumped out. The rear wall 8 has in it a fill port area 43, defined by a cut line 45, which stops short of meeting, to leave an integral hinge area 44. Such fill ports are conventional.

To reiterate what has been described above, in erecting the box, the front and rear walls are folded upwardly to the position shown in FIG. 7, the front and rear wall end flaps 34 and 30 are folded in to the position shown in FIG. 6, the side walls 12 and 13 are folded upright as shown in FIG. 6, the screen 50 is placed over the end wall flaps, and the side wall panels are folded over the screen 50 and the end wall flaps. The lower edges of the side wall flaps are pushed toward the end flaps until the locking tabs 27 pass over the slits 5, depressing the bottom wall adjacent the end flaps to expose a lip defining an inboard edge of the slits, against which the locking tabs abut. The top wall 6 is then folded along the top edge of the rear wall 8, to lie closely against the hinge areas 23 along the top of the side walls, the closure panel 15 is folded over the front wall, and the tuck-in tabs 17 are pushed between the front wall end flaps and the side walls, where they are snugly frictionally held. The tuck-in tabs are preferably so made as to abut the underside of the hinge area 23 when they are pushed between the front wall flaps and the side walls until the closure panel is flush against the front wall 10, positively to hold the top wall firmly against the outer surface of the hinge area 23. Strips of tape are placed over the side edges of the top wall and the adjacent side walls, and a short strip of tape, over the meeting edge of the closure panel, front wall and bottom wall. That strip can be oriented at right angles to the meeting edge, because it is only to ensure that the closure panel does not move away from the front wall. The insects to be transported are poured into the box thorough the filling port 43, and the port secured by a piece of tape. When the box is to be emptied, the piece of tape over the bottom edge of the closure panel is cut, the closure flap is opened, withdrawing the tuck-in tabs, the finger opening area is pushed in, a finger inserted through the opening and behind the front wall, and the front wall is torn along the tear lines 40, the rest of the box maintaining its integrity. One reason for this arrangement is that, conventionally, communicating compartments, open at opposite ends adjacent the front and rear walls, are placed in the box before the top wall is closed.

Numerous variations in the construction and method of erection and use of the box of this invention, within the scope of the appended claims, will occur to those skilled in the art in light of the foregoing disclosure. Merely by way of example, a single opening can be provided in the side walls, although the provision of the intervening column as described has advantages of strength and support for the screen. An additional tear line can be made in the front wall along its juncture with the bottom wall, and the finger opening area placed adjacent one side wall, so that the front wall tears along the bottom, the opposite tear line either remaining or being eliminated. The box can be made in any size desired for its purpose. The skirt 26 can be omitted, although it serves a useful purpose as a barrier for the insects and in providing frictional engagement with the bottom wall. The fill port can be formed in the front wall, eliminating the need for tape over the filling port when the box has been filled. The fill port can then take the place of the finger opening. Although the close fit of the closure panel over the front wall should make it unnecessary, it then may be thought desirable to put a strip of tape along the bottom edge of the closure panel. Although provision for opening the box as described is preferred, and has the advantage of ease of access, it is not absolutely essential that the front panel be equipped with a tear line. If no provision is made for opening the front panel, access to the interior of box can be had by cutting any tape along the edges that would interfere, swinging the front panel out and opening the top of the box. These variations are merely illustrative.

Having thus described the invention, what is claimed and desired to be secured by Letters Patent is:

1. A cricket box comprising a bottom wall; a top wall; a rear wall integral with said bottom wall along a bottom edge and integral with said top wall along an upper edge; a front wall integral with said bottom wall along a bottom edge; side walls integral with said bottom wall along a bottom edge, each of said side walls having at least one substantial opening in it; said rear and front walls having end flaps at each end, folded inwardly substantially perpendicularly to said front and rear walls to lie alongside and inboard of said side walls, said end flaps each being of a length to extend substantially to the center of the side wall it is alongside and having openings complementary to said side wall opening or openings; said side walls having side wall panels integral with the side walls, folded over said end flaps, said side wall panels having openings complementary to the opening or openings in said side walls and said front and rear wall end flaps, said side wall panels engaging said bottom wall along their outer edges, and screen caged between said side wall panels and said front and rear wall end flaps, and extending over said opening or openings.

2. The box of claim 1 including a closure panel integral along one edge with said top wall, folded over and contiguous said front wall, and tuck-in tabs, integral with side edges of said closure flap at its forward end, inserted between said side walls and said front wall end flaps.

3. The box of claim 1 wherein said front wall has tear lines from the bottom wall to the free upper edge of said front wall to permit the front wall to be torn open to release the contents of said box.

4. A cricket box comprising a bottom wall; a top wall; a rear wall integral with said bottom wall along a bottom edge and integral with said top wall along an upper edge; a front wall integral with said bottom wall along a bottom edge, said front wall having tear lines extending from the bottom wall to a free upper edge of said front wall to permit the front wall to be torn open to release the contents of said box and a finger opening area immediately below said upper edge of said front wall, defined by an interrupted cut line extending to said upper edge to facilitate tearing of said front wall when said area is opened; side walls integral with said bottom wall along a bottom edge, each of said side walls having in it two openings separated by an intermediate column; said rear and front walls having end flaps at each end, folded inwardly substantially perpendicularly to said front and rear walls and bottom to lie alongside said side walls, said end flaps having openings intermediate their lengths complementary to said side wall openings; said side walls having two rows of score lines, spaced and parallel, to define a hinge area; side wall panels integral with said side walls along the more outward of said score lines, folded over said end flaps, said side wall panels having openings complementary to the openings in said side walls and said end flaps, said side wall panels having at their free edges, a bottom wall-engaging strip integral with said side wall panel, extending inboardly of said box from said side wall panel, and locking tabs die cut from said bottom engaging strips at their junctions with the side wall panels and positioned to engage a slit-defining lip of a slit in the said bottom wall when said side wall panels are pushed into position contiguous said front and rear wall end flaps; screen caged between said side wall panels and said end flaps, extending over said openings; a closure panel integral along one edge with said top wall, folded over and contiguous said front wall, and tuck-in tabs, integral with side edges of said closure panel, inserted in spaces between said side walls and said front wall end flaps.

5. A blank for forming a cricket box, comprising a bottom wall; a top wall; a rear wall integral with said bottom wall along a fold line at an inner edge and integral with said top wall along a fold line along an outer edge; a front wall integral with said bottom wall along a fold line along an inner edge and having tear lines extending from said bottom wall to an outer edge; side walls integral with said bottom wall along a fold line along an inner edge, each of said side walls having two substantial openings in it; separated by a column said rear and front walls having, along fold lines, end flaps at each end, said end flaps being of a length to extend with leading edges adjacent one another behind said column but not to overlap and having openings complementary to said side wall openings; said side walls having side wall panels integral with the side walls along one of two spaced hinge lines in said side walls, adapted to be folded over said end flaps to cage screen between said side wall panels and said end flaps, to form, in effect, a three ply side wall with the screen between the side wall panel and the two plies made up by the end flaps and the side wall, said side wall panels having openings complementary to the openings in said side walls and said end flaps.

6. A method of erecting a cricket box from the blank of claim 5, comprising folding said front and rear walls to a position perpendicular to the bottom wall, folding the end flaps to a position perpendicular to the front and rear walls, folding the side walls to a position perpendicular to the bottom wall and along and outside the end flaps, positioning a screen along the inside surface of the end flaps, folding the side panels over the screen, providing a strip along an inner edge of each side wall panel, and folding the strip to a position in engagement with the bottom wall and substantially perpendicular to the side panels by pushing the side panels toward the end flaps.

7. A cricket box comprising a bottom wall; a top wall; a rear wall integral with said bottom wall along a bottom edge and integral with said top wall along an upper edge; a front wall integral with said bottom wall along a bottom edge; side walls integral with said bottom wall along a bottom edge, each of said side walls having at least one substantial opening in it; said rear and front walls having end flaps at each end, folded inwardly substantially perpendicularly to said front and rear walls to lie alongside and inboard of said side walls, said end flaps having openings complementary to said side wall opening or openings; said side walls having side wall panels integral with the side walls, folded over said end flaps, said side wall panels having openings complementary to the opening or openings in said side walls and said front and rear wall end flaps, said side wall panels engaging said bottom wall along their outer edges, and screen caged between said side wall panels and said front and rear wall end flaps, and extending over said opening or openings, said front wall having tear lines from the bottom wall to the free upper edge of said front wall to permit the front wall to be torn open to release the contents of said box and a finger opening area immediately below an upper edge of said front wall, defined by an interrupted cut line extending to said upper edge to facilitate tearing of said front wall when said finger area is opened.

8. The box of claim 7 including a fill port area in said rear wall defined by a cut line interrupted by an integral hinge.

9. The box of claim 1 wherein two openings are provided in each of said side walls, separated by an intermediate column, both said front wall and said back wall end flaps having corresponding openings entirely intermediate their length and extending with leading edges adjacent one another behind said column, and said side wall panels having corresponding openings.

\* \* \* \* \*